(12) United States Patent
Ni et al.

(10) Patent No.: US 11,007,214 B2
(45) Date of Patent: *May 18, 2021

(54) COMPOSITIONS AND METHODS FOR TREATING EYE DISEASES

(71) Applicant: CLOUDBREAK THERAPEUTICS LLC, Irvine, CA (US)

(72) Inventors: Jinsong Ni, Irvine, CA (US); Rong Yang, Irvine, CA (US)

(73) Assignee: CLOUDBREAK THERAPEUTICS LLC, Irvine, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/115,186

(22) Filed: Dec. 8, 2020

(65) Prior Publication Data

US 2021/0093657 A1 Apr. 1, 2021

Related U.S. Application Data

(63) Continuation of application No. PCT/US2020/037751, filed on Jun. 15, 2020.

(60) Provisional application No. 62/903,898, filed on Sep. 22, 2019, provisional application No. 62/869,133, filed on Jul. 1, 2019.

(51) Int. Cl.
| | |
|---|---|
| *A61K 31/724* | (2006.01) |
| *A61P 27/04* | (2006.01) |
| *A61P 27/02* | (2006.01) |
| *A61K 47/12* | (2006.01) |
| *A61K 9/08* | (2006.01) |
| *A61K 9/06* | (2006.01) |
| *A61K 47/02* | (2006.01) |
| *A61K 9/00* | (2006.01) |

(52) U.S. Cl.
CPC .......... *A61K 31/724* (2013.01); *A61K 9/0048* (2013.01); *A61K 9/06* (2013.01); *A61K 9/08* (2013.01); *A61K 47/02* (2013.01); *A61K 47/12* (2013.01); *A61P 27/02* (2018.01); *A61P 27/04* (2018.01)

(58) Field of Classification Search
None
See application file for complete search history.

(56) References Cited

U.S. PATENT DOCUMENTS

| | | | | |
|---|---|---|---|---|
| 5,851,777 | A * | 12/1998 | Hunter | G01N 33/553 |
| | | | | 435/7.1 |
| 7,491,743 | B2 * | 2/2009 | Cuny | A61P 37/04 |
| | | | | 514/397 |
| 9,937,188 | B2 | 4/2018 | Trogden et al. | |
| 2005/0250737 | A1 | 11/2005 | Hughes et al. | |
| 2017/0266220 | A1 | 9/2017 | Young et al. | |
| 2018/0085392 | A1 * | 3/2018 | Gaspar | A61K 9/08 |
| 2018/0098937 | A1 | 4/2018 | Horn | |
| 2019/0328772 | A1 * | 10/2019 | Priestley | A61K 9/06 |

FOREIGN PATENT DOCUMENTS

| | | | |
|---|---|---|---|
| WO | 2019068763 A1 | 4/2019 | |
| WO | 2020047146 A1 | 3/2020 | |
| WO | WO-2020072621 A1 * | 4/2020 | ............ C11D 7/268 |

OTHER PUBLICATIONS

Stefánsson, E., Thórisdóttir, S., Gudmundsson, Ó. G . . . & Kristinsson, J. K. (1996). 2-Hydroxypropyl-β-Cyclodextrin in Eye Drops. Evaluation of Artificial Tear-Drops In Human Patients. In Proceedings of the Eighth International Symposium on Cyclodextrins (pp. 391-394). (Year: 1996).*
AndroGel: Highlights of Prescribing Information, AbbVie Inc., North Chicago, IL 60064, USA (2013).

* cited by examiner

*Primary Examiner* — Dale R Miller
(74) *Attorney, Agent, or Firm* — SZDC Law P.C.

(57) ABSTRACT

A method for treating an eye disease of an affected eye includes administering to the affected eye of a subject in need of such treatment a steroidal-androgen-free composition containing a therapeutically effective amount of beta-cyclodextrin derivative. The eye disease can be meibomian gland dysfunction, blepharitis, or dry eye disease. A steroidal-androgen-free composition includes a beta-cyclodextrin derivative as a sole active pharmaceutical ingredient. The steroidal-androgen-free composition is an ophthalmic composition.

10 Claims, 5 Drawing Sheets

COMPOSITIONS AND METHODS FOR TREATING EYE DISEASES

The present invention is a Continuation Application of PCT/US2020/037751, filed on Jun. 15, 2020, which claims priority to U.S. Provisional Application No. 62/869,133, filed on Jul. 1, 2019, and 62/903,898, filed on Sep. 22, 2019, both of which are incorporated by reference for all purposes as if fully set forth herein.

FIELD OF THE INVENTION

The present invention relates to compositions and methods for treating meibomian gland dysfunction (MGD), blepharitis, dry eye disease and related ocular indications of an affected eye. The invention also relates to compositions for artificial tears or eye lubricants.

BACKGROUND OF THE INVENTION

Meibomian glands are a type of sebaceous gland located in the tarsal plate of the upper and lower eyelids. These glands are responsible for the supply of meibum, an oily substance that prevents evaporation of the eye's tear film, prevents tear evaporation, and makes the closed lids airtight. There are approximately 50 glands on the upper eyelids and 25 glands on the lower eyelids. Meibomian glands are distinguished by grape-like clusters of acini on the mucocutaneous lid junction and empty their lipid content (meibum) at this junction in order to coat the ocular surface via holocrine secretion. The glands are anchored by cells that produce both polar and nonpolar lipids, which are then stored in lysosomes that merge into larger storage granules. As these cells continue to enlarge with lipid, they eventually commit apoptosis and rupture to release the meibum into the meibomian gland opening and spill the meibum over the ocular surface. Meibum is fluid at the temperature of ocular surface, and distributed over the ocular surface in a thin, smooth film on top of the aqueous layer. This lipid layer prevents evaporation of the aqueous layer. Alterations in the meibum composition, property and level can have a profound effect on the health of the eyelid margins and ocular surface. Meibomian gland dysfunction in the general population is pretty high with some estimates as high as 39% with an increase in incidence in contact lens wearers.

Meibomian gland secretions form the lipid layer of tears and consist of polar and nonpolar lipids. The lipid composition of the meibum can affect tear parameters like initial formation of a composite monolayer with polar and nonpolar phases, adequate fluidity near body temperature, and the ability to undergo compression and expansion during blinking. These properties are very important for effective polar lipid structuring and fluidity (melted physical state) at normal body temperature. Any alterations in the saturation of the fatty acids can lead to instability of tears.

MGD patients usually have normal production of aqueous tears by their lacrimal glands, their meibomian glands can atrophy and this is frequently accompanied by metaplasia of the ductal epithelium of these glands. Anterior erosion of the mucocutaneous junction of the eyelid is often noted, as well as eyelid and conjunctival infection, eyelid margin irregularity, corneal epithelial changes, and corneal vascularization. In some cases, abnormal overproduction of meibum can also cause the same problems.

As meibomian glands lining the eyelids produce lipids that promote the stability of the tears and reduce evaporation of the tear film, dysfunction of the meibomian glands can lead to lipid insufficiency that destabilizes the tear film and causes decreases in tear film break-up time and evaporative dry eye.

MGD may also be characterized by increased melting point of the lipids, causing solidification of the lipids and obstruction of the meibomian gland secretion. This can result in cysts, infections and decreased lipid content in the tears. MGD is also characterized by excess, abnormally turbid secretion that gets inspissated and plugs the meibomian orifices. This is followed by metaplasia of the meibomian ducts (abnormal hyper-keratinization). Blockage and resistance to flow results in inflammation and vascularization (redness) of tissues around the orifice. Inflammatory mediators accumulate in the tear film leading to damage of ocular surface. Sequalae of all these events is inflammatory scarring of the duct leading to stenosis. Initially glands swell and eventually atrophy.

Common complaints of MGD patients include blurred or filmy vision, light sensitivity or photophobia, burning or foreign body sensations in the eye, excessive tearing, intolerance to contact lens and pain.

Light sensitivity is an intolerance of sunlight, fluorescent light or incandescent light. It is one of the symptoms of MGD and is associated with other conditions such as corneal abrasion, uveitis, meningitis, a detached retina, contact lens irritations, sunburn or refractive surgery.

Blurred vision is a lack of sharpness of vision, and may result from abnormalities such as nearsightedness, farsightedness, presbyopia, and astigmatism. It is also associated with MGD and other ocular surface conditions.

Currently, various lipid based artificial tears or lubricants are used to alleviate the symptoms of MGD. Physical treatments, such as maintaining good hygiene, heating, and massage, are often used as well. However, these treatments do not cure the disease. There is a need for an effective and safe treatment for MGD.

Among MGD patients, blepharitis and dry eye disease are frequent as a direct or indirect result of MGD. These conditions share many of the same symptoms discussed above and are considered as indications related to MGD. Both these conditions are very complicated with multifactorial causes. They are briefly described in the following sections.

Blepharitis is inflammation of the eyelids that usually affects both eyes along the edges of the eyelids. It is a condition that can develop at later stages of MGD or independent of MGD. MGD causes posterior blepharitis when meibomian glands are clogged and engorged. Commonly, this is associated with acne rosacea, and hormonal causes are suspected. Anterior blepharitis is caused by bacterial infections and can be treated with antibiotics. Both anterior and posterior blepharitis may be caused by a *Demodex* mite. The exact pathophysiology of blepharitis is multifactorial and is still not very clear. Patients with blepharitis often have symptoms observed in MGD and dry eye disease, including itching, burning, and crusting of the eyelids. They may also experience tearing, blurred vision and foreign body sensation.

Dry eye disease (DED) is a condition in which a person doesn't have enough quality tears to lubricate and nourish the eye. Tears are necessary for maintaining the health of the front surface of the eye and for providing clear vision. Dry eye is a common and often chronic problem. The prevalence worldwide is estimated from 5% to 34%. Inadequate amount or quality of tear is the cause of DED. Tear production diminishes with age, with various medical conditions or as a side effect of certain medicines. Environmental conditions, such as wind and dry climates, can also decrease tear volume due to increased tear evaporation. When the normal amount of tear production decreases or tears evaporate too quickly from the eyes due to abnormal meibum lipid, symptoms of dry eye disease can develop. The DED mainly caused by reduced tear production is defined as aqueous-deficient DED. The DED caused by increased tear evaporation is defined as evaporative DED. The latter is the majority, but many patients have mixed causes.

Most of the current DED treatment aim to attenuate the immune responses. This invention focuses on the improvement tear film stability to attack one of the early pathological events of the disease.

SUMMARY OF THE INVENTION

In one embodiment, a method for treating an eye disease of an affected eye includes administering to the affected eye of a subject in need of such treatment a steroidal-androgen-free composition containing a therapeutically effective amount of beta-cyclodextrin derivative. The beta-cyclodextrin derivative is an active pharmaceutical ingredient for treating the eye disease, and the beta-cyclodextrin derivative is a sole active pharmaceutical ingredient for treating the eye disease.

In another embodiment, the eye disease is one selected from the group consisting of a meibomian gland dysfunction, a blepharitis, and a dry eye disease.

In another embodiment, the steroidal-androgen-free composition is administered topically to the affected eye or topically onto a surrounding skin of the affected eye.

In another embodiment, the beta-cyclodextrin derivative is selected from the group consisting of (2-hydroxypropyl)-beta-cyclodextrin, methyl-beta-cyclodextrin, 6-monodeoxy-6-monoazido-beta-cyclodextrin, 6-monodeoxy-6-monoiodo-beta-cyclodextrin, 6-monodeoxy-6-monothio-beta-cyclodextrin, 6-monodeoxy-O-(p-toluenesulfonyl)-beta-cyclodextrin, 6-monodeoxy-6-monoazido-6-mono-O-(p-toluenesulfonyl)-beta-cyclodextrin, 6-monodeoxy-6-monobromo-beta-cyclodextrin, heptakis(2,3,6-tri-O-benzoyl)-beta-cyclodextrin, heptakis(2,3,6-tri-O-methyl)-beta-cyclodextrin, heptakis(2,6-di-O-methyl)-beta-cyclodextrin, heptakis(6-deoxy-6-azido)-beta-cyclodextrin, heptakis(6-deoxy-6-chloro)-beta-cyclodextrin, heptakis(6-deoxy-6-bromo)-beta-cyclodextrin, heptakis(6-deoxy-6-iodo)-beta-cyclodextrin, heptakis(6-deoxy-6-thio)-beta-cyclodextrin, sulfobutylated beta-cyclodextrin, acetyl beta-cyclodextrin, carboxymethyl-beta-cyclodextrin, succinyl-beta-cyclodextrin, (2-carboxyethyl)-beta-cyclodextrin, sulfobutylated beta-cyclodextrin, 6-monodeoxy-6-mono-amino-beta-cyclodextrin, heptakis(6-deoxy-6-amino)-beta-cyclodextrin, (2-hydroxy-3-N,N,N-trimethylamino)propyl-beta-cyclodextrin, heptakis(2,3,-di-O-methyl)-hexakis(6-O-methyl)-6-monodeoxy-6-monoamino ta-beta-cyclodextrin, 6-monodeoxy-6-monoamino-random-methyl-beta-cyclodextrin, (2-hydroxy-3-N,N,N-trimethylamino)propyl-beta-cyclodextrin, heptakis(6-sulfo)-beta-cyclodextrin, heptakis (2,3-di-O-acetyl-6-sulfo) beta cyclodextrin, heptakis(2,3-di-O-methyl-6-sulfo)-beta-cyclodextrin, heptakis(2,3-di-O-methyl-6-deoxy-6-amino)-beta-cyclodextrin, heptakis(2,3-di-O-methyl-6-deoxy-6-azido)-beta-cyclodextrin, heptakis (6-deoxy-6-(2-carboxyethyl)thio)-beta-cyclodextrin, and a combination thereof.

In another embodiment, the beta-cyclodextrin derivative is present in the composition at a concentration of 0.1% w/w to 30% w/w, 0.5% w/w to 25% w/w, 1% w/w to 20% w/w, 5% w/w to 15% w/w, 8% w/w to 12% w/w, about 10% w/w, or 10% w/w.

In another embodiment, the steroidal-androgen-free composition does not include an androgen with a steroidal chemical structure, testosterone, or precursors of testosterone.

In another embodiment, the method further includes maintaining effects of treating the meibomian gland dysfunction for a period of time post administering.

In another embodiment, the period of time post administering is 1 month, 2 months, 3 months, 4 months, 5 months, 6 months, 7 months, 8 months, 9 months, 10 months, 11 months or 12 months.

In another embodiment, the method further includes dissolving lipids crystals deposited at the opening of the meibomian gland of the affected eye; and increasing tear film stability.

In another embodiment, the method further includes one selected from the group consisting of: reducing the sensation of a foreign body in the affected eye, hyperemia or redness of the affected eye and eyelid margin, plugging of a meibomian gland orifice of the affected eye, inflammation of ocular tissues, corneal staining of the affected eye, burning sensation in the affected eye, photophobia, blurred vision, pain in the affected eye, or itchiness in the affected eye; increasing tear film break up time (TBUT); improving astigmatism; decreasing the phase transition temperature of meibum; improving clinical signs and symptoms of meibomian gland dysfunction (MGD); and a combination thereof. The ocular tissues are selected from the group consisting of meibomian glands, ducts, orifices, eye lids, cornea, and conjunctiva.

In another embodiment, a steroidal-androgen-free composition includes a beta-cyclodextrin derivative as a sole active pharmaceutical ingredient. The steroidal-androgen-free composition is an ophthalmic composition.

In another embodiment, the steroidal-androgen-free composition consists essentially of the beta-cyclodextrin derivative and one or more ingredients selected from the group consisting of hydroxypropyl guar, xantham gum, trehalose, sodium chloride, castor oil, cremophor ELP, Polysorbate 80, HPMC 2910, edetate disodium, glycerin, a buffer agent, and water.

In another embodiment, the buffer agent is selected from the group consisting of sodium phosphate monobasic monohydrate, citric acid, and sodium citrate.

In another embodiment, the beta-cyclodextrin derivative is present in the steroidal-androgen-free composition at a concentration of 0.1% w/w to 30% w/w.

In another embodiment, in this steroidal-androgen-free composition, the beta-cyclodextrin derivative is selected from the group describe above.

In another embodiment, the steroidal-androgen-free composition is a solution, a suspension, an emulsion, a gel, an ointment, or a cream.

In another embodiment, the steroidal-androgen-free composition is an artificial tear or a lubricant.

In another embodiment, a steroidal-androgen-free composition consists of a beta-cyclodextrin derivative, sodium chloride, a buffer agent, and water.

In another embodiment, in this steroidal-androgen-free composition, the beta-cyclodextrin derivative is selected from the group describe above.

In another embodiment, the buffer agent is selected from the group consisting of sodium phosphate monobasic monohydrate, citric acid, and sodium citrate.

In another embodiment, the steroidal-androgen-free composition consists of 5%-20% of the beta-cyclodextrin derivative, 0.20%-0.80% of sodium chloride, 0.10-0.30% of sodium phosphate monobasic monohydrate, and water.

It is to be understood that both the foregoing general description and the following detailed description are exemplary and explanatory and are intended to provide further explanation of the invention as claimed.

BRIEF DESCRIPTION OF THE DRAWINGS

The accompanying drawings, which are included to provide a further understanding of the invention and are incorporated in and constitute a part of this specification, illustrate embodiments of the invention and together with the description serve to explain the principles of the invention.

In the drawings.

DETAILED DESCRIPTION OF THE ILLUSTRATED EMBODIMENTS

Reference will now be made in detail to embodiments of the present invention, example of which is illustrated in the accompanying drawings.

The present invention provides compositions and treatment methods for treating meibomian gland dysfunction (MGD), blepharitis and dry eye disease. Without being bound by a particular theory, the methods utilize two important properties of the cyclodextrin derivatives: 1) the ability to sequester and dissolve cholesterol and 2) the ability to inhibit immune activities such as macrophage activation. The first ability will help to remove excess lipids deposited near the orifice of meibomian gland and help the flow of lipid and it will also modify the meibum composition to make it more fluid at the normal temperature of the ocular surface. The second ability will attenuate the abnormal immune activity present on the eyes of MGD patients. These patients suffer increased cytokines and immune cell activities, including macrophages, T-cells. Unlike the current treatments for MGD, this invention will have the potential to modify the disease in addition to improve symptoms such as light sensitivity and blurred vision.

Cyclodextrins belong to the family of cyclic oligosaccharides, consisting of a macrocyclic ring of glucose subunits joined by α-1,4-glycosidic bonds. Cyclodextrins may contain a number of glucose monomers ranging from six to eight units in a ring, creating a cone shaped molecule. Natural cyclodextrins include alpha-, beta- and gamma-cyclodextrins, corresponding to 6, 7, and 8 glucose units, respectively. The number of the glucose units is important for biological and non-biological activities associated with these molecules. This application discloses surprise findings on cholesterol binding abilities in relation to the number of glucose units. The inventors of the present application discovered that the 7-unit beta-cyclodextrins, but not the 6- and 8-unit alpha- and gamma-cyclodextrins, can have significant binding of cholesterol.

Natural cyclodextrins can be chemically modified by additions of other groups, e.g., hydroxypropyl, methyl groups, to create "cyclodextrin derivatives." The cyclodextrin derivatives can have different physical and chemical properties and behave differently when interacting with other molecules. This discloses a surprise finding on how different modifications groups in cyclodextrin derivatives determine the abilities of cyclodextrin derivatives to dissolve cholesterol in water. The methyl derivatives of beta-cyclodextrin have the best ability to dissolve cholesterol in water, followed by hydroxypropyl derivatives. As discussed below, the rank order findings of various cyclodextrin derivatives will support the composition and method application.

The disclosure is based on the surprise finding by the inventors that only certain derivatives of the beta type of cyclodextrin have the significant ability to sequester and dissolve cholesterol. Another surprise finding is that certain modifications of the beta-cyclodextrin is more effective than others in cholesterol sequestration. These surprise findings are the basis of the disclosure wherein selected derivatives of a selected cyclodextrin is used as compositions and methods for treating MGD, blepharitis and dry eye disease. Specifically, beta-cyclodextrin derivatives used herein can be (2-hydroxypropyl)-beta-cyclodextrin, methyl-beta-cyclodextrin, 6-monodeoxy-6-monoazido-beta-cyclodextrin, 6-monodeoxy-6-monoiodo-beta-cyclodextrin, 6-monodeoxy-6-monothio-beta-cyclodextrin, 6-monodeoxy-O-(p-toluenesulfonyl)-beta-cyclodextrin, 6-monodeoxy-6-mono-azido-6-mono-O-(p-toluenesulfonyl)-beta-cyclodextrin, 6-monodeoxy-6-monobromo-beta-cyclodextrin, heptakis(2,3,6-tri-O-benzoyl)-beta-cyclodextrin, heptakis(2,3,6-tri-O-methyl)-beta-cyclodextrin, heptakis(2,6-di-O-methyl)-beta-cyclodextrin, heptakis(6-deoxy-6-azido)-beta-cyclodextrin, heptakis(6-deoxy-6-chloro)-beta-cyclodextrin, heptakis(6-deoxy-6-bromo)-beta-cyclodextrin, heptakis(6-deoxy-6-iodo)-beta-cyclodextrin, heptakis(6-deoxy-6-thio)-beta-cyclodextrin, sulfobutylated beta-cyclodextrin, acetyl beta-cyclodextrin, Carboxymethyl-beta-cyclodextrin, Succinyl-beta-cyclodextrin, (2-carboxyethyl)-beta-cyclodextrin, sulfobutylated beta-cyclodextrin, 6-monodeoxy-6-mono-amino-beta-cyclodextrin, heptakis(6-deoxy-6-amino) beta-cyclodextrin, (2-hydroxy-3-N,N,N-trimethylamino)propyl-beta-cyclodextrin, heptakis(2,3,-di-O-methyl)-hexakis(6-O-methyl)-6-monodeoxy-6-monoamino-beta-cyclodextrin, 6-monodeoxy-6-monoamino-random-methyl-beta-cyclodextrin, (2-hydroxy-3-N,N,N-trimethylamino)propyl beta-cyclodextrin, heptakis(6-sulfo)-beta-cyclodextrin, heptakis(2,3-Di-O-acetyl-6-sulfo) beta cyclodextrin, heptakis(2,3- di-O-methyl-6-sulfo) beta cyclodextrin, heptakis(2,3-di-O-methyl-6-deoxy-6-amino) beta cyclodextrin, heptakis(2,3-di-O-methyl-6-deoxy-6-azido) beta-cyclodextrin, heptakis(6-deoxy-6-(2-carboxyethyl)thio) beta-cyclodextrin or a combination thereof.

U.S. Pat. No. 9,937,188 (Allergan, Inc) discloses the use of formulations comprising testosterone or related androgens for the treatment of keratoconjunctivitis sicca and meibomian gland disease. In this patent, cyclodextrin acts as a solubilizer for testosterone, the active ingredient, and is disclosed as one of the inactive excipients that also include castor oil, C10-30 alkyl acrylate crosspolymer and Polyoxyl 40 stearate. The methods of the present application are fundamentally different in two respect: 1) certain derivatives of cyclodextrin, not cyclodextrin in general is disclosed here for the compositions and methods; 2) the disclosed compounds are used as the active ingredient for the treatment of MGD and related disease, not as an inactive excipient of a formulation as disclosed in U.S. Pat. No. 9,937,188. Importantly, the disclosed method does not use any steroidal androgen as disclosed in U.S. Pat. No. 9,937,188. This key difference will avoid many of the potential steroidal-related side effects, such as virilization for females and stimulation of the prostate for males. Androgens control the development, differentiation, and function of male reproductive and accessory sex tissues. Testosterone regulates the expression of thousands of genes in ocular tissues. Such gene regulations in meibomian gland provides the beneficial effects disclosed in U.S. Pat. No. 9,937,188, but since a very large number of genes' expression are changed, side effect potential is also high. ANDROGEL, containing 1% testosterone as an active ingredient, was approved for topical use as a replacement therapy in males for conditions associated with a deficiency or absence of endogenous testosterone. ANDROGEL product insert indicates the worsening of benign prostatic hyperplasia (BPH) and potential risk of prostate cancer for patients with BPH. ANDROGEL 1% should be avoided for unintentional exposure to women or children. Secondary exposure to testosterone can produce signs of virilization and ANDROGEL 1% should be discontinued until the cause of virilization is identified. Other observed side effects in the clinical trials of ANDROGEL 1% included azoospermia, edema with or without congestive heart failure, sleep apnea. Serum testosterone, prostate specific antigen, hemoglobin, hematocrit, liver function tests and lipid concentrations should be monitored periodically for patients treated with ANDROGEL 1%. The present application excludes the use of testosterone and uses cyclodextrin as the sole active ingredient. This avoids the side effect issues associated with testosterone.

As used herein, the "ophthalmic compositions" are useful for placement onto the surface of an eye of a human or animal. Such compositions are preferably administered into an eye of a patient in a fluid form. By administering the compositions as a fluid, the administration may occur without forming an incision in the eye. As used herein, the "transdermal compositions" deliver a therapeutically effective amount of active ingredient across the skin of a patient. Transdermal compositions typically involve a carrier (such as a liquid, gel, or solid matrix, or a pressure sensitive adhesive) into which the active ingredient to be delivered is incorporated.

As used herein, an "active pharmaceutical ingredient" refers to therapeutic agents or substances used to treat a medical ophthalmic disease or condition of the eye and/or to otherwise beneficially affect a patient's eye, and "sole active pharmaceutical ingredient" refers to the one and only therapeutic agent or substance used to treat a medical ophthalmic disease or condition of the eye and/or to otherwise beneficially affect a patient's eye.

The beta-cyclodextrin derivatives described herein are the sole active pharmaceutical ingredient of the ophthalmic compositions. The ophthalmic compositions do not include any other active pharmaceutical ingredients for treating eye diseases. Specifically, the ophthalmic compositions do not include an androgen with a steroidal chemical structure, testosterone, or precursors of testosterone. The ophthalmic compositions may include one or more inactive ingredients selected from the group consisting of hydroxypropyl guar, xantham gum, trehalose, sodium chloride, castor oil, cremophor ELP, Polysorbate 80, HPMC 2910, edetate disodium, glycerin, and a buffer agent. The ophthalmic compositions may be a water-based formulation.

As used herein, the term "therapeutically effective amount" is intended to mean a nontoxic but sufficient concentration or amount of a beta-cyclodextrin derivative, and more specifically, a beta-cyclodextrin derivative selected from the group described above, to provide the desired therapeutic effects. The amount that is effective will vary from subject to subject, depending on the age and general condition of the individual, the cyclic polysaccharide, and the like. Thus, it is not always possible to specify an exact effective concentration or amount. However, an appropriate effective amount in any individual case may be determined by one of ordinary skill in the art using routine experimentation. Furthermore, the exact effective amount of a beta-cyclodextrin derivative incorporated into a composition or dosage form of the present invention is not critical, so long as the concentration is within a range sufficient to permit ready application of the solution or formulation so as to deliver an amount of beta-cyclodextrin derivative-including compound that is within a therapeutically effective range.

2-Hydroxypropyl-beta-cyclodextrin (2-HP-β-CD) (CAS Number: 128446-35-5) is a modified cyclodextrin derivative, and has the following formula I. 2,6-Di-O-methyl-beta-cyclodextrin (also known as heptakis(2,6-di-O-methyl)-beta-cyclodextrin, CAS Number 51166-71-3) is a modified cyclodextrin derivative, and has the following formula II.

In a clinical trial to study a drug for treating pterygium, a surprising discovery was made that the vehicle (2-HP-β-CD Formulation I) reduced the symptom of foreign body sensation, pain, redness and in particular, light sensitivity and blurred vision in pterygia patients. Pterygium is a common ocular disorder that causes several ocular symptoms that are also common in MGD. They are also common in disease such as blepharitis and dry eye disease. The meibomian glands in pterygium area are often dysfunctional. In this clinical trial, several common ocular symptoms including irritation, foreign body sensation, pain, light sensitivity and blurred vision, were assessed using questionnaires to the patients. Surprisingly, overall ocular symptom scores combining the scores of irritations, foreign body sensation, pain, light sensitivity and blurred vision have significantly reduced during cyclodextrin treatment when comparing to the prior treatment baseline. In particular, light sensitivity and blurred vision were significantly improved by the vehicle during the treatment compared to the prior treatment baseline. Even more surprising is that these symptom relief effects maintained for a prolong period of 5 months post vehicle treatment. The vehicle's main ingredient was 10% 2-HP-β-CD (w/w).

Compositions and methods for treating ocular symptoms are disclosed. The methods include administration of a suitable ocular formulation containing 2-Hydroxypropyl beta Cyclodextrin (2-HP-β-CD) to patients in need thereof. The disclosed methods are used for sustained improvements on the overall symptoms associated with MGD, blepharitis and dry eye disease.

EXAMPLES

The invention is further described in the following representative examples, which do not limit the scope of the claimed invention.

Example 1: 2-HP-β-CD Formulation I

The formulation in this example includes 5%-20% (preferably, 10%) 2-HP-β-CD (w/w), 0.10-0.30% (preferably, 0.16%) sodium phosphate monobasic monohydrate (w/w), 0.20-0.80% (preferably, 0.52%) sodium chloride (w/w), and water. The formulation has a pH value of 4-9 (preferably, 7.4).

Example 2: Application of 2-HP-β-CD Formulation I

A Phase 2a Multicenter, Randomized, Vehicle-Controlled, Dose Escalating Study was carried out to evaluate the Safety, Efficacy and Pharmacokinetics of Nintedanib Ophthalmic Solution in Patients with Primary or Recurrent Pterygium. 2-HP-β-CD Formulation I was used as vehicle.

The multicenter, randomized, double-masked, vehicle-controlled, parallel study was conducted with 28 days three times a day (TID) repeat ocular dosing of vehicle and 0.2% nintedanib, followed by 5-month post-dosing observation.

Figure 1:
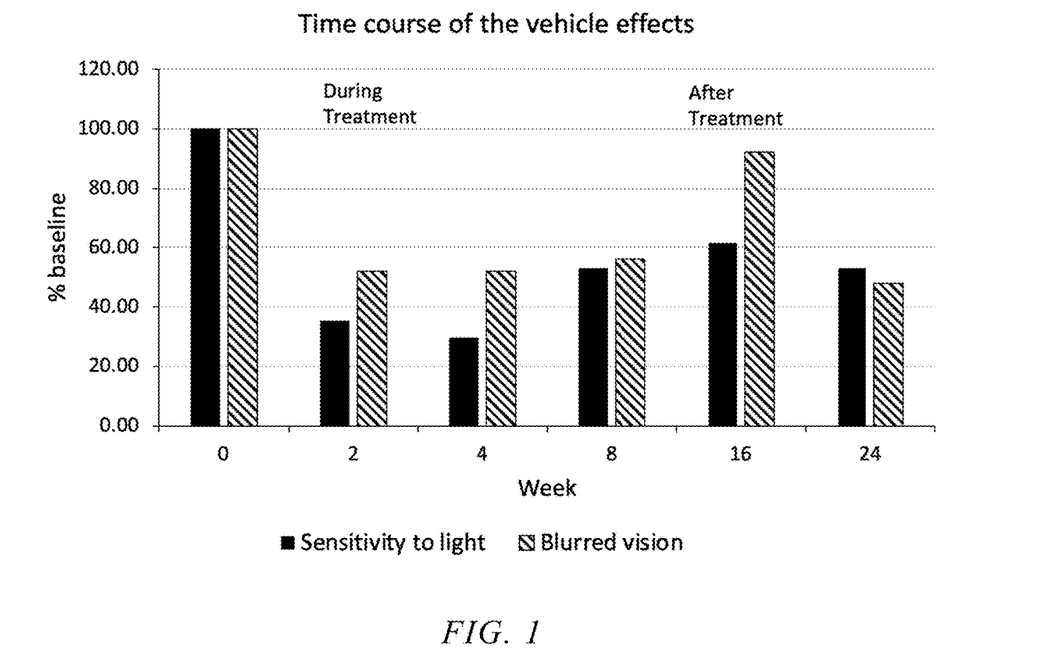
FIG. 1 shows the effects of 2-hydroxypropyl-beta-cyclodextrin (2-HP-β-CD) on sensitivity to light and blurred vision over a 24-week period in a Phase 2 clinical trial.

Results:

In the clinical trial, pterygia patients were asked 15 questions on ocular sign, symptom and quality of life. Surprisingly, the 2-HP-β-CD Formulation I caused an unexpected improvement on light sensitivity and blurred vision. Table 1 shows that the two symptoms were statistically improved during treatment at weeks 2 and 4. A trend of effects also remained after the stop of treatment at weeks 8, 16, and 24. The results are shown in FIG. 1. The other questions didn't generate statistically significant effects.

TABLE 1

Effects of the 2-HP-β-CD Formulation I on sensitivity to light and blurred vision

| | Sensitivity to light | | | | | |
|---|---|---|---|---|---|---|
| | Day 1 | Wk 2 | Wk 4 | Wk 8 | Wk 16 | Wk 24 |
| Mean veh (n = 23) | 0.74 | 0.26 | 0.22 | 0.39 | 0.45 | 0.39 |
| SD | 1.14 | 0.45 | 0.42 | 0.72 | 0.96 | 0.72 |
| TTEST vs baseline | | 0.031 | 0.015 | 0.148 | 0.167 | 0.175 |
| | Blurred vision | | | | | |
| Mean veh (n = 23) | 1.09 | 0.57 | 0.57 | 0.61 | 1.00 | 0.52 |
| SD | 1.31 | 1.20 | 0.95 | 1.03 | 1.23 | 0.51 |
| TTEST vs baseline | | 0.004 | 0.025 | 0.086 | 0.776 | 0.039 |

Example 3: 2-HP-β-CD Formulation II

The formulation in this example includes 0.1-05% Castor Oil (w/w), 0.1-1.0% Polysorbate 80, super-refined (w/w), 0.1-1.0% Cremophor ELP (w/w), 5-20% 2-HP-β-CD (w/w), 0.010-0.30% Citric Acid (w/w), 0.030-0.060% Sodium Citrate (w/w), 0.01-1.0% HPMC 2910 (w/w), 0.01-0.5% Edetate Disodium (w/w), and water. The formulation has a pH value of 4.0-9.0. Glycerin is used to adjust the osmolality of the solution to 280-300 mOsm/kg.

Example 4: Application of 2-HP-β-CD Formulation II

A Phase 3 Multicenter, Randomized, Vehicle-Controlled, Dose Escalating Study will be carried out to evaluate the Safety, Efficacy and Pharmacokinetics of Nintedanib Ophthalmic Solution in Patients with Primary or Recurrent Pterygium. 2-HP-β-CD Formulation II will be used as vehicle.

Figure 2:
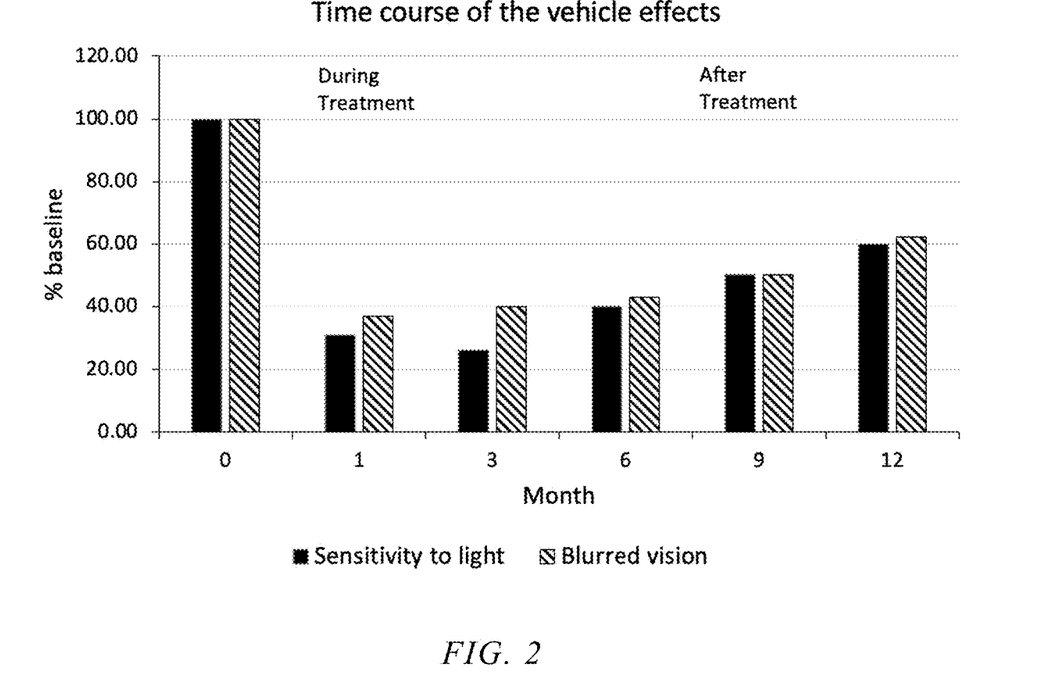
FIG. 2 shows the effects of 2-HP-β-CD on sensitivity to light and blurred vision over a 12-month period in a Phase 2 clinical trial.
Figure 3:
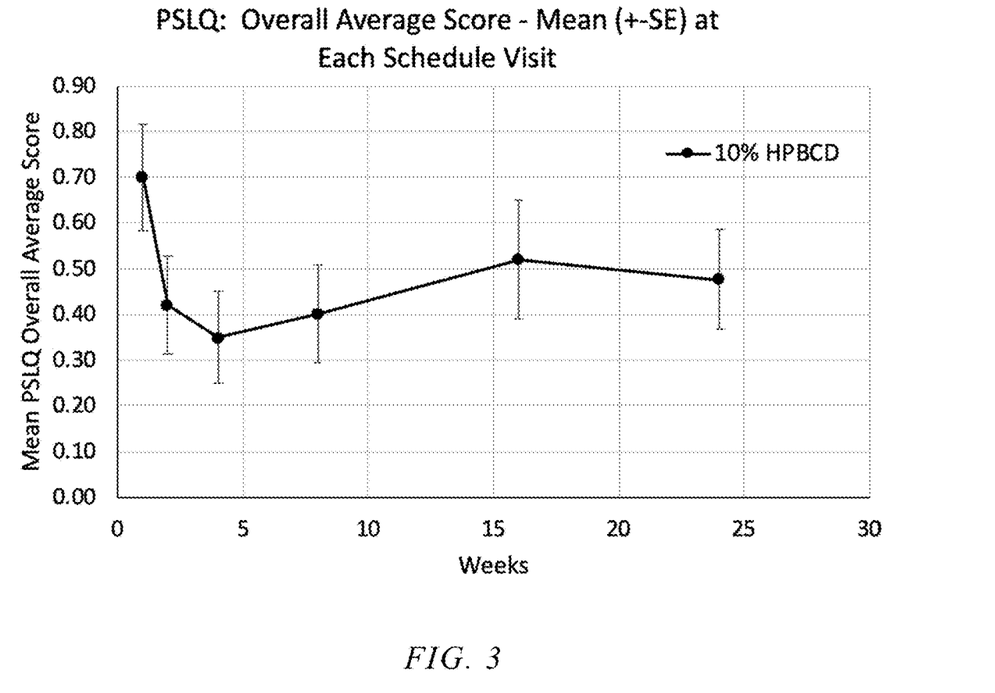
FIG. 3 shows the overall average score of patients treated in the disease eye with a topical ocular drop of 2-hydropropyl-beta-cyclodextrin formulation at a concentration of 10% (w/w), 3 times daily for 4 weeks with subsequent continuous observations for 5 months in a Phase 2 clinical trial.
Figure 4:
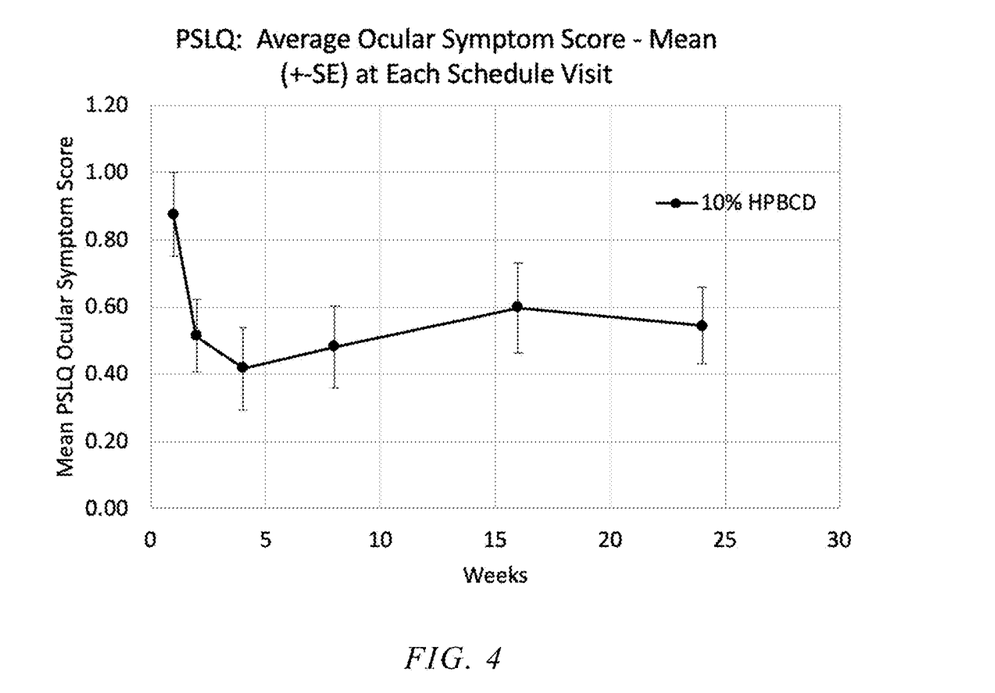
FIG. 4 shows the average ocular symptom score of the patients in a Phase 2 clinical trial.
Figure 5:
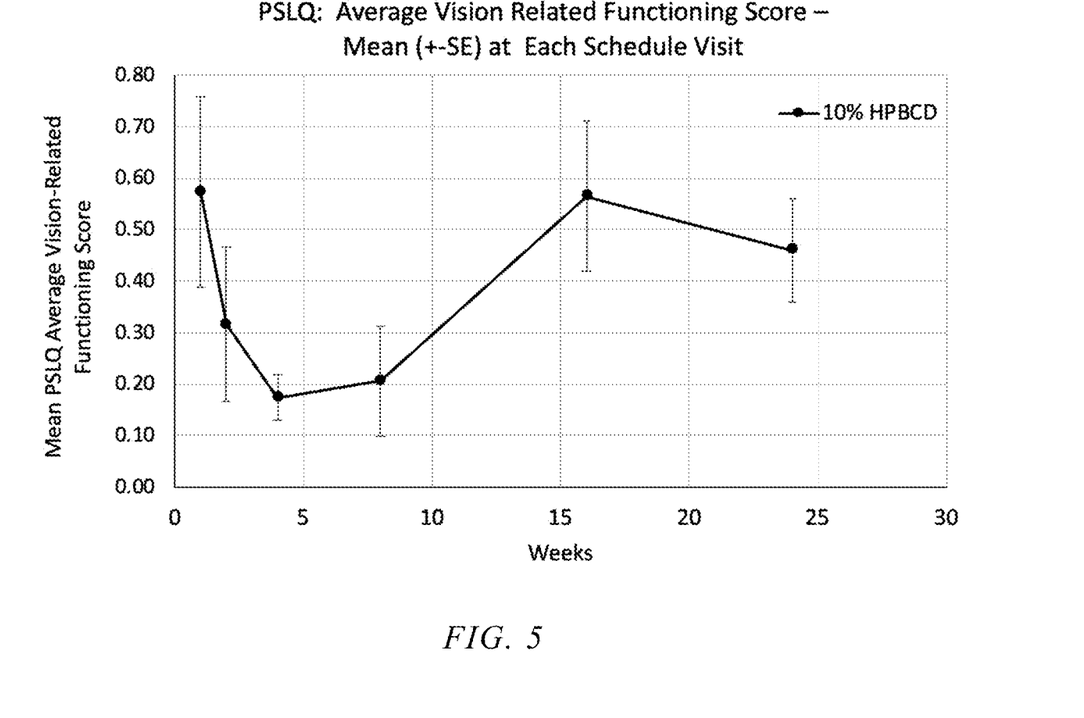
FIG. 5 shows the average vision-related functioning score in a Phase 2 clinical trial.
Figure 6:
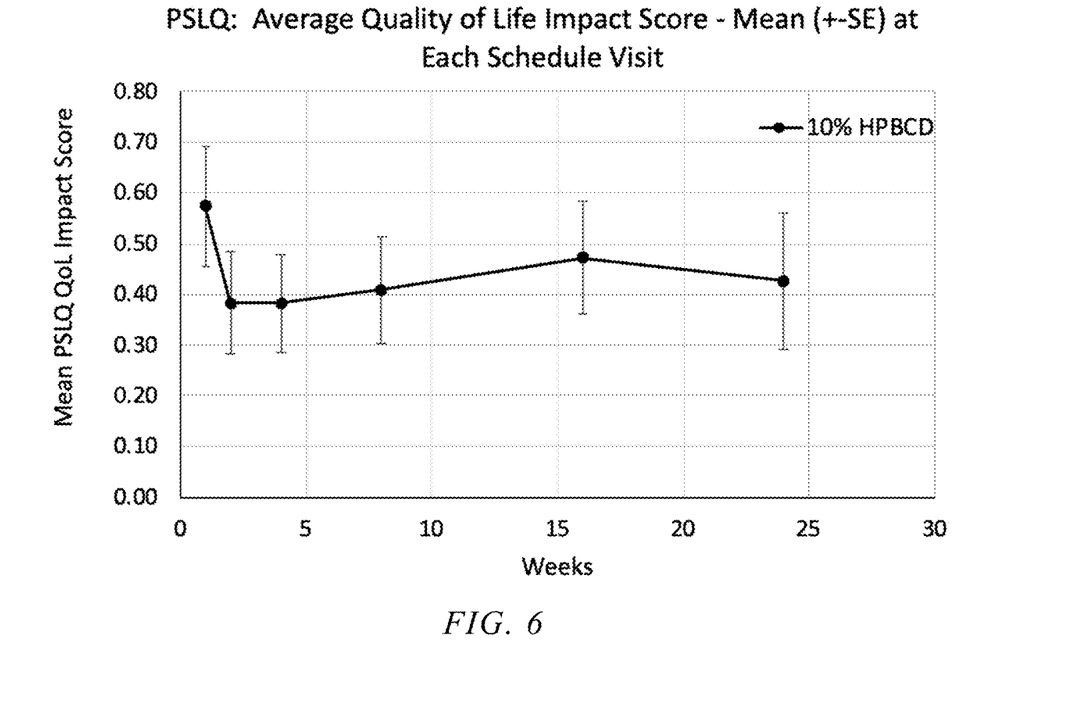
FIG. 6 shows the average quality of life impact score of the patients in a Phase 2 clinical trial.

The treatment time of the Phase 3 trial is longer than that of the Phase 2a trial. The results are shown in FIG. 2.

Example 5: Application of 2-HP-β-CD Formulation I

A Phase 2a Multicenter, Randomized, Vehicle-Controlled, Dose Escalating Study was carried out to evaluate the Safety, Efficacy and Pharmacokinetics of Nintedanib Ophthalmic Solution in Patients with Primary or Recurrent Pterygium. The multicenter, randomized, double-masked, vehicle-controlled, parallel study was conducted with 28 days three times a day (TID) repeat ocular dosing of vehicle and 0.2% nintedanib, followed by 5-month post-dosing observation. 2-HP-β-CD formulation listed in Example 1 was used as the vehicle.

Pterygium patients often have meibomian gland atrophy and clinical signs and symptoms of MGD, including ocular pain, itchy, foreign body sensation, redness, sensitivity to light and blue vision. In the Phase II clinical trial, pterygia patients were asked 15 questions on ocular symptom, vision-related functioning and quality of life via Pterygium Symptom and Life Quality (PSLQ) questionnaires.

Results:

PSLQ analyses were performed for 4 average category scores; Overall, Ocular Symptoms, Vision-Related Functioning, and Quality of Life Impact. Results of the analyses are summarized in Table 2 through Table 5. 2-HP-β-CD-treated group showed significant improvements in PSLQ scores when compared to the baseline. Statistically significant changes (improvements) from baseline were detected in the 2-HP-β-CD-treated group at Weeks 2, 4, and 8 for Overall PSLQ scores and at Weeks 2, 4 and 8 for Ocular Symptom scores, and at Week 2 for Quality of Life Impact scores and at Weeks 4 and 8 for the Vision-Related Functioning scores.

Surprisingly, the improvements on ocular symptoms and vision-related functioning were not only observed during 2-HP-β-CD treatment period at Weeks 2 and 4, but also continued after 2-HP-β-CD treatment period at Week 8.

TABLE 2

PSLQ: Overall Average Score - Baseline and Changes from Baseline at Each Follow-up Visit: Modified Intent-to-Treat Population

| Timepoint Statistic | 2-HP-β-CD (N = 23) |
|---|---|
| Baseline | |
| Mean (SD) | 0.70 (0.66) |
| Change from Baseline at Week 2 | |
| Mean (SD) | −0.28 (0.45) |
| p-value [a] | 0.007 |
| Change from Baseline at Week 4 | |
| Mean (SD) | −0.35 (0.51) |
| p-value [a] | 0.004 |
| Change from Baseline at Week 8 | |
| Mean (SD) | −0.30 (0.55) |
| p-value [a] | 0.016 |
| Change from Baseline at Week 16 | |
| Mean (SD) | −0.20 (0.64) |
| p-value [a] | 0.164 |
| Change from Baseline at Week 24 | |
| Mean (SD) | −0.22 (0.73) |
| p-value [a] | 0.158 |

[a] Within treatment group change from baseline p-value based on the one sample t-test.

TABLE 3

PSLQ: Average Ocular Symptom Score - Baseline and Changes from Baseline at Each Follow-up Visit: Modified Intent-to-Treat Population

| Timepoint Statistic | 2-HP-β-CD (N = 23) |
|---|---|
| Baseline | |
| Mean (SD) | 0.88 (0.81) |
| Change from Baseline at Week 2 | |
| Mean (SD) | −0.36 (0.69) |
| p-value [a] | 0.019 |
| Change from Baseline at Week 4 | |
| Mean (SD) | −0.46 (0.71) |
| p-value [a] | 0.005 |
| Change from Baseline at Week 8 | |
| Mean (SD) | −0.39 (0.84) |
| p-value [a] | 0.035 |
| Change from Baseline at Week 16 | |
| Mean (SD) | −0.29 (0.79) |
| p-value [a] | 0.102 |
| Change from Baseline at Week 24 | |
| Mean (SD) | −0.33 (0.90) |
| p-value [a] | 0.090 |

[a] Within treatment group change from baseline p-value based on the one sample t-test.

TABLE 4

PSLQ: Average Vision-Related Functioning Score - Baseline and Changes from Baseline at Each Follow-up Visit: Modified Intent-to-Treat Population

| Timepoint Statistic | 2-HP-β-CD (N = 23) |
|---|---|
| Baseline | |
| Mean (SD) | 0.57 (0.80) |
| Change from Baseline at Week 2 | |
| Mean (SD) | −0.27 (0.65) |
| p-value [a] | 0.067 |
| Change from Baseline at Week 4 | |
| Mean (SD) | −0.48 (0.65) |
| p-value [a] | 0.003 |
| Change from Baseline at Week 8 | |
| Mean (SD) | −0.43 (0.62) |
| p-value [a] | 0.004 |
| Change from Baseline at Week 16 | |
| Mean (SD) | −0.23 (0.56) |
| p-value [a] | 0.08 |
| Change from Baseline at Week 24 | |
| Mean (SD) | −0.11 (1.1) |
| p-value [a] | 0.617 |

[a] Within treatment group change from baseline p-value based on the one sample t-test.

TABLE 5

PSLQ: Average Quality of Life Impact Score - Baseline and Changes from Baseline at Each Follow-up Visit: Modified Intent-to-Treat Population

| Timepoint Statistic | 2-HP-β-CD (N = 23) |
|---|---|
| Baseline | |
| Mean (SD) | 0.57 (0.92) |
| Change from Baseline at Week 2 | |
| Mean (SD) | −0.19 (0.39) |
| p-value [a] | 0.029 |
| Change from Baseline at Week 4 | |
| Mean (SD) | −0.19 (0.50) |
| p-value [a] | 0.082 |
| Change from Baseline at Week 8 | |
| Mean (SD) | −0.17 (0.52) |
| p-value [a] | 0.140 |
| Change from Baseline at Week 16 | |
| Mean (SD) | −0.13 (0.68) |
| p-value [a] | 0.392 |
| Change from Baseline at Week 24 | |
| Mean (SD) | −0.15 (0.59) |
| p-value [a] | 0.239 |

[a] Within treatment group change from baseline p-value based on the one sample t-test.

Further analysis was done to assess the potential therapeutic effect of 10% 2-hydroxypropyl beta-cyclodextrin on patients with symptoms of ocular pain, itchy, foreign body sensation, redness, sensitivity to light and blurred vision. These ocular symptoms are often observed in MGD patients. Scores of these symptoms were graded by patients as part of PSLQ questionnaires.

Figure 7:
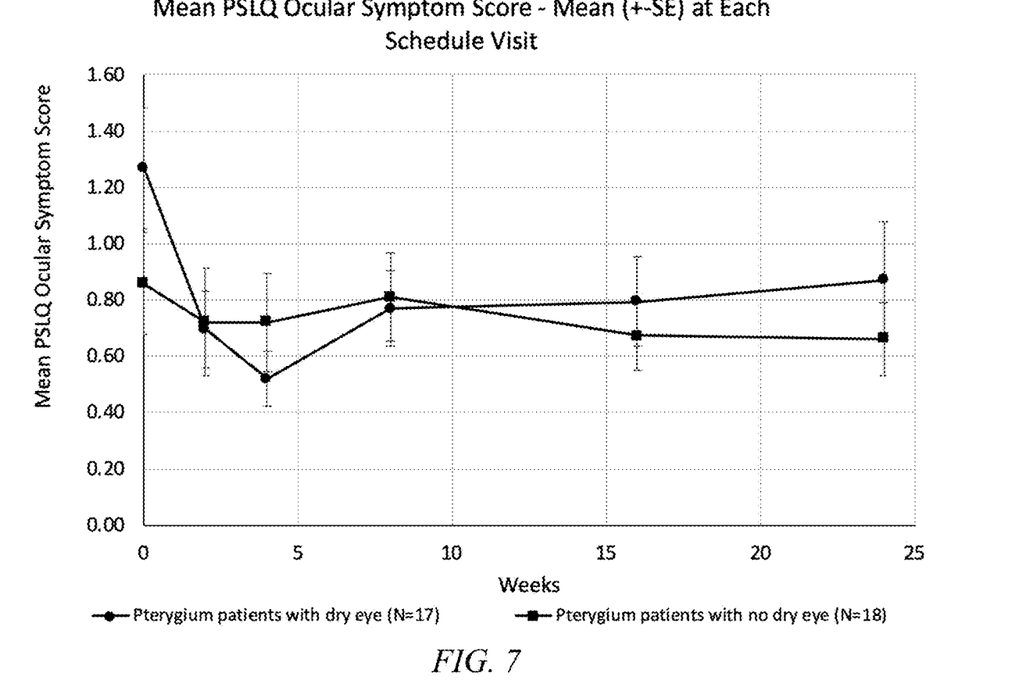
FIG. 7 shows ocular symptom score at each schedule visit for pterygium patients with dry eye or with no dry eye in a Phase 2 clinical trial.
Figure 8:
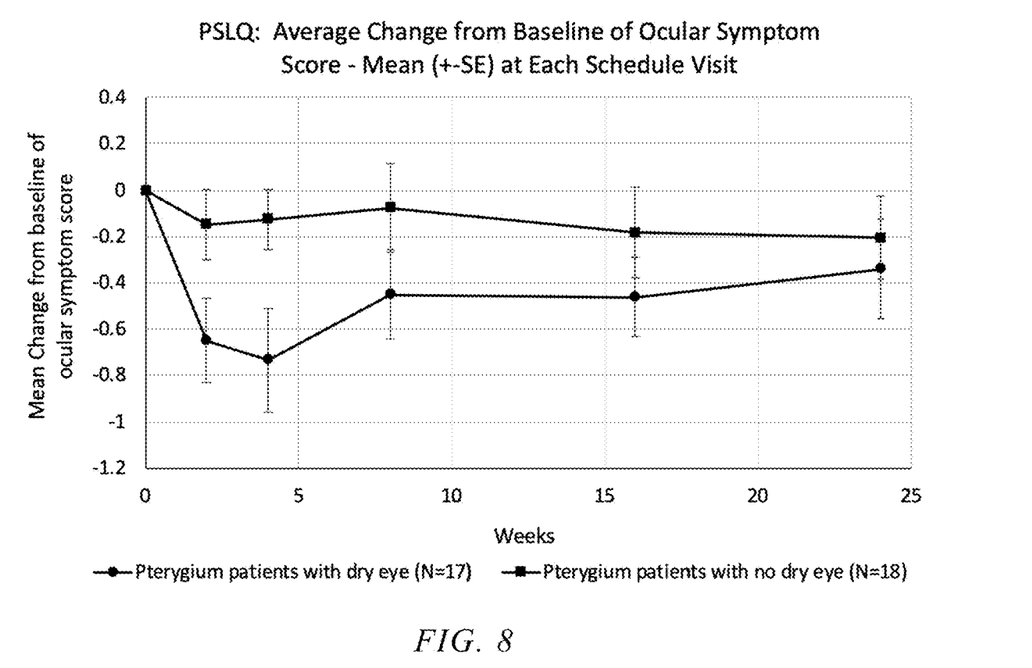
FIG. 8 shows average change from baseline of ocular symptom score at each schedule visit for pterygium patients with dry eye or with no dry eye in a Phase 2 clinical trial.

(1) Dry eye patients vs. Non-dry eye patients (based upon patients' medical history) with the combined nintedanib-treated and vehicle-treated groups. Results: Dry eye patients vs. Non-dry eye patients on Ocular Symptom Score as part of PSLQ: FIG. 7 shows mean PSLQ ocular symptom score at each schedule visit for pterygium patients with dry eye or with no dry eye and FIG. 8 shows average change from baseline of ocular symptom score at each schedule visit for pterygium patients with dry eye or with no dry eye.

The pterygium patients with dry eye condition was compared with pterygium patients with no dry eye condition. In this comparison, all pterygium patients with dry eye condition in the drug and vehicle treated group was combined and the same was done for pterygium patients with no dry eye condition. Number of data points for each group were N=17 for dry eye and N=18 for no dry eye. The data showed that statistically significant differences at Week 2 (p=0.042) and Week 4 (p=0.025) between dry eye group and no dry eye group. The mean differences in PSLQ ocular symptom reduction were 0.50 at Week 2 and 0.61 at Week 4. Pterygium patients with dry eye condition had higher baseline score and had bigger reduction from baseline of ocular symptom score during treatment period when compared to pterygium patients with no dry eye condition.

Figure 9:
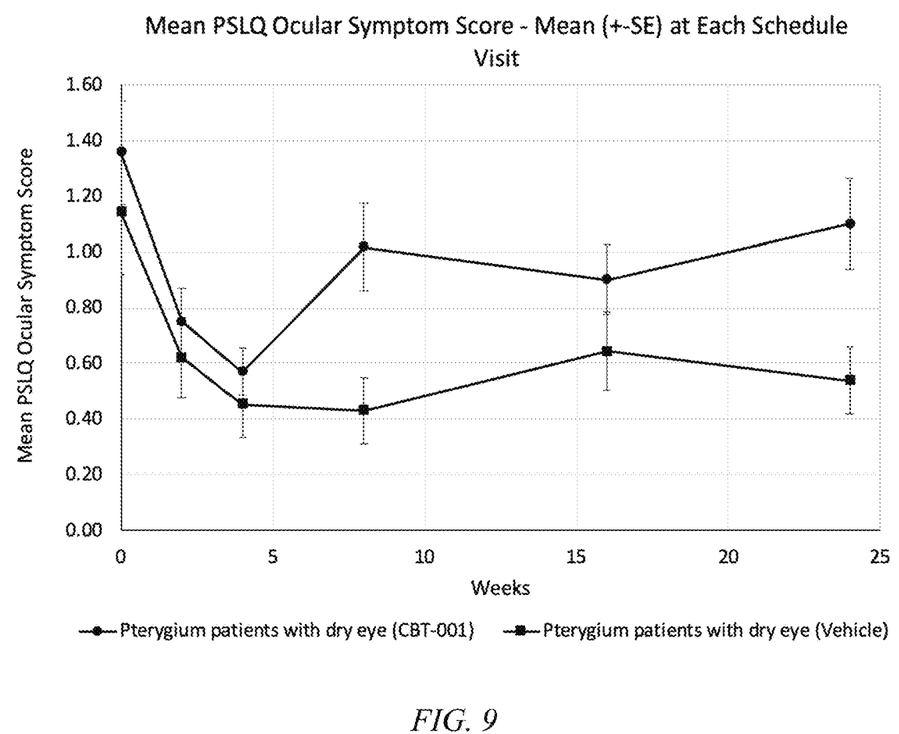
FIG. 9 shows ocular symptom score at each schedule visit for pterygium patients with dry eye in a Phase 2 clinical trial.
Figure 10:
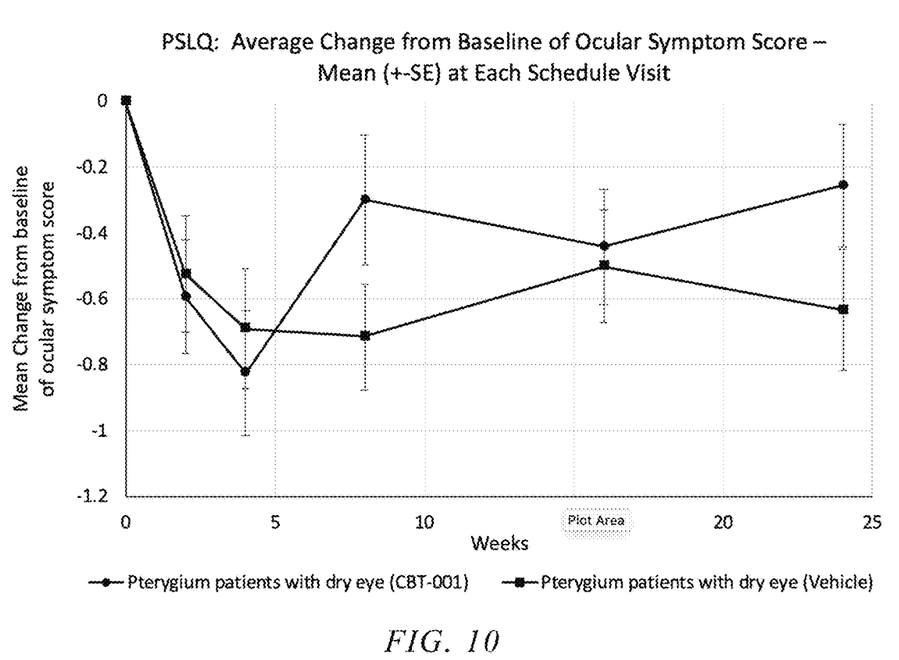
FIG. 10 shows average change from baseline of ocular symptom score at each schedule visit for pterygium patients with dry eye in a Phase 2 clinical trial.

(2) Nintedanib vs. Vehicle for dry eye patients (based upon patients' medical history). Results: Nintedanib vs. Vehicle in Dry eye patients on Ocular Symptom Score as part of PSLQ: FIG. 9 shows mean PSLQ ocular symptom score at each schedule visit for pterygium patients with dry eye and FIG. 10 shows average change from baseline of ocular symptom score at each schedule visit for pterygium patients with dry eye.

Pterygium patients with dry eye condition in the drug treated group and vehicle treated group had similar responses for PSLQ ocular symptom. The change from baseline for PSLQ ocular symptom was similar during the treatment period and no statistically significant differences observed at any timepoints.

In conclusion: the evidences support that 10% 2-hydroxypropyl-beta-cyclodextrin had effects on PSLQ responses from pterygium patients with dry eye condition and pterygium patients with no dry eye condition. The magnitude of reduction in PSLQ ocular symptom score was statistically significant bigger in pterygium patients with dry eye condition than in pterygium patients with no dry eye condition.

On the contrary, when compared pterygium patients with dry eye condition that were treated with Nintedanib 0.2% or Vehicle, there was no statistically significant differences between two treatment groups. This indicates Nintedanib 0.2% was not the main cause for the reduction in PSLQ scores in pterygium patients with dry eye condition while 10% 2-hydroxypropyl-beta-cyclodextrin was the major factor that caused reduction in PSLQ scores in the pterygium patients with dry eye condition.

Example 6: Solubility of Cholesterol in Cyclodextrin

Solubility of cholesterol in the presence of cyclodextrin (CD) has been measured and reported (Nishijo, J., Moriyama, S. and Shiota S., Chem. Pharm. Bull., 51(11) 1253-1257, 2003). Solubility of Cholesterol in the Presence of CD Aliquots (7.0 ml) of CD aqueous solution of the appropriate concentration and excess cholesterol were placed in 20 ml L-type test tubes and the tubes were sealed. The test tubes were kept at 10, 25, 37 and 45° C., respectively, with shaking, for 1 week until solubility equilibrium was achieved. Then the solution was filtered through the membrane and 3.0 ml of color-producing reagent was added to 0.1 ml of the filtrate. Then the reaction mixture was heated for 5 min at 37° C. and the absorbance at 600 nm was measured using the calibration curve made in advance. Stability of cholesterol-CD complex was determined by a Shimadzu RF-503A fluorescence spectrophotometer at 25° C. Table 6 shows the increase in absorbance due to cholesterol dissolved by CDs in aqueous solution at 37° C.

TABLE 6

Increase in Absorbance Due to Cholesterol Dissolved by CDs in Aqueous Solution at 37° C.

| CD [a] | Absorbance (600 nm) |
|---|---|
| Without CD | 0 |
| Alpha-CD | 0 |
| Beta-CD | 0 |
| Gamma-CD | 0 |
| HP-beta-CD | 0.01 |
| DOM-beta-CD | 0.336 |

[a] Concentration of CDs added is $1.0 \times 10^{-2}$ M.

As shown in Table 6, in the presence of alpha-CD, beta-CD and gamma-CD, the absorbances were zero, suggesting that these CDs do not form soluble complexes with cholesterol in aqueous solution. While only a slight increase in absorbance was observed in the presence of HP-beta-CD, a remarkable increase in absorbance was observed in the presence of DOM-beta-CD. These results suggest that DOM-beta-CD has a strong ability to form soluble complex with cholesterol in aqueous solution, but HP-beta-CD only a weak ability. Although soluble complex formations of cholesterol with alpha-CD, beta-CD and gamma-CD were not detected, insoluble complex formation might occur.

Example 7: Safety of 10% HP-β-CD (the Vehicle in the Phase 2 Clinical Trial)

This example demonstrated the safety of HP-β-CD in human. The data was derived from the stage 2 of the Phase 2 clinical trial in pterygium patients who were topically administered 10% HP-β-CD as the vehicle of the testing article. The patients were treated for 4 weeks with three-time a day dosing and then followed up for another 20 weeks after the stop of treatment. The safety evaluation included the 20 weeks of non-treatment period. The example showed the vehicle results and not the testing article that was not relevant to this application.

All safety analyses were conducted on the safety population. MedDRA nomenclature was used to code adverse events. The number and percent of patients reporting adverse events were tabulated based on preferred terms and/or system organ class. Summary tables were generated for all adverse events regardless of causality as well as for treatment-related adverse events.

The mean duration of exposure to study treatment was 28 days with 96% of patients having a treatment duration of at least 28 days (Table 7).

TABLE 7

Extent of Exposure to Study Treatment Safety Population

| Exposure | Vehicle (N = 25) |
|---|---|
| Treatment duration (days) | |
| Mean | 28.0 |
| SD | 0.0 |
| Median | 28.0 |
| Min, Max | 28, 28 |
| n | 24 |
| Treatment duration, n (%) | |
| >= 1 day | 24 (96.0) |
| >= 14 days | 24 (96.0) |
| >= 28 days | 24 (96.0) |
| Missing | 1 (4.0) |

Adverse Events

A summary of adverse events was presented in Table 8. Ocular treatment-emergent adverse events (TEAEs) of any causality were reported in the study eyes of 16.0% (4/25) of patients in the Vehicle group. There were no study discontinuations due to AEs. No deaths or drug-related serious adverse events were reported in the study.

TABLE 8

Summary of Adverse Events Safety Population

| | Vehicle (N = 25) n (%) |
|---|---|
| All Ocular TEAEs | |
| Study Eye | 4 (16.0) |
| Non-study Eye | 0 |
| Treatment Related Ocular TEAEs | |
| Study Eye | 1 (4.0) |
| Non-study Eye | 0 |
| All Non-ocular TEAEs | 7 (28.0) |
| Treatment Related Non-ocular TEAEs | 0 |
| Serious TEAEs | 1 (4.0) |
| Treatment-related Serious TEAEs | 0 |
| Discontinuation due to adverse events | 0 |
| Deaths | 0 |

In summary, 10% HP-β-CD as the vehicle in the Phase 2 pterygium clinical trial showed excellent safety profile, with only one treatment-related TEAE reported.

Example 8: Screening of Various Cyclodextrin (CD) and CD Derivatives for Ability to Dissolve Cholesterol in Water Purpose: To determine the level of cholesterol that can be dissolved in water when 10 different CDs and their derivatives were added at three concentrations.

Methods: CDs tested were: alpha-cyclodextrin (ACD), beta-cyclodextrin (BCD), gamma-cyclodextrin (GCD), 2-hydroxypropyl-alpha-cyclodextrin (HP-ACD), 2-hydroxypropyl-beta-cyclodextrin (HP-BCD), 2-hydroxypropyl-gamma-cyclodextrin (HP-GCD), random methyl-beta-cyclodextrin (M-BCD), heptakis (2,6-di-O-methyl)-beta-cyclodextrin (DM-BCD), 6-O-alpha-maltosyl-beta-cyclodextrin (6-AM-BCD), and sulfobutylated beta-cyclodextrin (SBE-BCD).

All CD solutions were prepared with starting 20% (w/v) solutions by accurately adding about 800 mg CDs in 4 milliliter water, 1% and 10% were diluted from this 20% solution to 2 mL for each sample preparation experiment.

Cholesterol was added accurately to all CD water solutions at about 40 mg/mL or about 80 mg per 2 mL. This amount of cholesterol was enough to fully saturate the CD solutions with white settlements or floating or both. All samples were conditioned at ambient by shaking using a rotator for 5 days.

After the equilibration with shaking for 5 days at ambient, the clear or semi-clear portion was filtered with 0.2 μm filter. 50 μL of the filtered solution was diluted with 450 μL methanol (10×) for HPLC analysis. NOVAPAK phenyl column (7.6 cm by 3.9 mm I.D.) was used with a mobile phase of acetonitrile: water (70:30) at a flow rate of 0.5 ml/min and detection at UV at 210 nm.

Results are summarized in Table 9.

TABLE 9

Cholesterol-dissolving activities of various CDs

| CD% (w/v) | M-BCD | DM-BCD | 6-AM-BCD | HP-BCD | SBE-BCD | BCD | HP-GCD | GCD | HP-ACD | ACD |
|---|---|---|---|---|---|---|---|---|---|---|
| 0 | 0.02 | 0.02 | 0.02 | 0.02 | 0.02 | 0.02 | 0.02 | 0.02 | 0.02 | 0.02 |
| 1 | 0.15 | 0.19 | 0.03 | 0.01 | 0.002 | ND | ND | ND | ND | ND |
| 10 | 6.03 | 5.13 | 2.57 | 0.82 | 0.03 | NA | 0.003 | ND | ND | ND |
| 20 | 14.2 | 10.43 | 3.38 | 2.98 | 0.15 | NA | 0.011 | ND | ND | ND |

Note:
ND = not detectable; NA = not tested.

All the natural unmodified CDs had no or extremely low ability (below method sensitivity) to dissolve cholesterol in water. The HP derivative showed unexpected large differences among alpha-, beta-, and gamma-CDs. HP-ACD had no detectable cholesterol dissolving activity and HP-GCD had extremely low levels, in contrast, HP-BCD had substantial ability to dissolve cholesterol.

Further research was focused on the BCD type and other derivatives of this type of CD. The results were surprising and unexpected: the ability of cholesterol dissolving ability was rank ordered as following: methyl→hydroxypropyl→sulfobutyl→unmodified (no activity). Among the methylated BDs, M-BCD and DM-BCD were similar and were the best, 6-Am-BCD was about half lower. For the CDs that showed cholesterol-dissolving activity, the CD concentrations were proportional to the activities.

Surprising Findings Summary:

1) Natural alpha-, beta- and gamma-CDs had no to very low ability to dissolve cholesterol in water.

2) For CD derivatives, only beta-CD derivatives showed substantial ability to dissolve cholesterol in water.

3) For the beta-CD derivatives, the rank order of ability was: methyl→hydroxypropyl→sulfobutyl-.

It will be apparent to those skilled in the art that various modifications and variations can be made in the present invention without departing from the spirit or scope of the invention. Thus, it is intended that the present invention cover the modifications and variations of this invention provided they come within the scope of the appended claims and their equivalents.

What is claimed is:

1. A method for treating meibomian gland dysfunction or blepharitis in an affected eye, comprising administering to the affected eye of a subject in need of such treatment a composition comprising, as sole active pharmaceutical ingredient for treating the meibomian gland dysfunction or blepharitis, a therapeutically effective amount of a beta cyclodextrin derivative.

2. The method of claim 1, wherein the composition is administered topically to the affected eye or topically onto a surrounding skin of the affected eye.

3. The method of claim 1, wherein the beta-cyclodextrin derivative is selected from the group consisting of (2-hydroxypropyl)-beta-cyclodextrin, methyl-beta-cyclodextrin, 6-monodeoxy-6-monoazido-beta-cyclodextrin, 6-monodeoxy-6-monoiodo-beta-cyclodextrin, 6-monodeoxy-6-monothio-beta-cyclodextrin, 6-monodeoxy-O-(p-toluenesulfonyl)-beta-cyclodextrin, 6-monodeoxy-6-monoazido-6-mono-O-(p-toluenesulfonyl)-beta-cyclodextrin, 6-monodeoxy-6-monobromo-beta-cyclodextrin, heptakis(2,3,6-tri-O-benzoyl)-beta-cyclodextrin, heptakis(2,3,6-tri-O-methyl)-beta-cyclodextrin, heptakis(2,6-di-O-methyl)-beta-cyclodextrin, heptakis(6-deoxy-6-azido)-beta-cyclodextrin, heptakis(6-deoxy-6-chloro)-beta-cyclodextrin, heptakis(6-deoxy-6-bromo)-beta-cyclodextrin, heptakis(6-deoxy-6-iodo)-beta-cyclodextrin, heptakis(6-deoxy-6-thio)-beta-cyclodextrin, sulfobutylated beta-cyclodextrin, acetyl beta-cyclodextrin, carboxymethyl-beta-cyclodextrin, succinyl-beta-cyclodextrin, (2-carboxyethyl)-beta-cyclodextrin, 6-monodeoxy-6-monoamino-beta-cyclodextrin, heptakis(6-deoxy-6-amino)-beta-cyclodextrin, (2-hydroxy-3-N,N,N-trimethylamino)propyl-beta-cyclodextrin, heptakis(2,3,-di-O-methyl)-hexakis(6-O-methyl)-6-monodeoxy-6-monoamino to-beta-cyclodextrin, 6-monodeoxy-6-monoamino-random-methyl-beta-cyclodextrin, (2-hydroxy-3-N,N,N-trimethylamino)propyl-beta-cyclodextrin, heptakis(6-sulfo)-beta-cyclodextrin, heptakis (2,3-di-O-acetyl-6-sulfo) beta cyclodextrin, heptakis(2,3-di-O-methyl-6-sulfo)-beta-cyclodextrin, heptakis(2,3-di-O-methyl-6-deoxy-6-amino)-beta-cyclodextrin, heptakis(2,3-di-O-methyl-6-deoxy-6-azido)-beta-cyclodextrin, heptakis(6-deoxy-6-(2-carboxyethyl)thio)-beta-cyclodextrin, and a combination thereof.

4. The method of claim 1, wherein the beta-cyclodextrin derivative is methyl-beta-cyclodextrin.

5. The method of claim 1, wherein the beta-cyclodextrin derivative is heptakis(2,6-di-O-methyl)-beta-cyclodextrin.

6. The method of claim 1, wherein the beta-cyclodextrin derivative is present in the composition at a concentration of 0.1% w/w to 30% w/w, 0.5% w/w to 25% w/w, 1% w/w to 20% w/w, 5% w/w to 15% w/w, 8% w/w to 12% w/w, about 10% w/w, or 10% w/w.

7. The method of claim 1, further comprising administering the composition in an amount sufficient to maintain effects of treating meibomian gland dysfunction during administration of the composition and for a period of time post administration of the composition.

8. The method of claim 7, wherein the period of time post administration is 1 month, 2 months, 3 months, 4 months, 5 months, 6 months, 7 months, 8 months, 9 months, 10 months, 11 months or 12 months.

9. The method of claim 1, further comprising administering the composition in an amount sufficient to:
dissolve lipid crystals deposited at an opening of a meibomian gland of the affected eye; and
increase tear film stability.

10. The method of claim 1, further comprising administering the composition in an amount sufficient to provide one selected from the group consisting of:
reducing sensation of a foreign body in the affected eye, hyperemia or redness of the affected eye and eyelid margin, plugging of a meibomian gland orifice of the affected eye, inflammation of ocular tissues, corneal staining of the affected eye, burning sensation in the affected eye, photophobia, blurred vision, pain in the affected eye, or itchiness in the affected eye;

increasing tear film break up time (TBUT);
improving astigmatism;
decreasing phase transition temperature of meibum;
improving clinical signs and symptoms of meibomian gland dysfunction (MGD); and
a combination thereof, wherein the ocular tissues are selected from the group consisting of meibomian glands, ducts, orifices, eye lids, cornea, and conjunctiva.

* * * * *